United States Patent [19]
Amino et al.

[11] Patent Number: 5,413,610
[45] Date of Patent: May 9, 1995

[54] ARTIFICIAL HIP JOINT

[75] Inventors: Hirokazu Amino; Yoshinori Shiraiwa, both of Kyoto, Japan; Ian C. Clarke, Santa Monica, Calif.

[73] Assignee: Kyocera Corporation, Kyoto, Japan

[21] Appl. No.: 38,552

[22] Filed: Mar. 26, 1993

Related U.S. Application Data

[63] Continuation of Ser. No. 370,450, Jun. 23, 1989, abandoned, Continuation-in-part of Ser. No. 136,398, Dec. 22, 1987, abandoned.

Foreign Application Priority Data

Dec. 25, 1986 [JP] Japan ............... 61-312551

[51] Int. Cl.⁶ .............................. A61F 2/32
[52] U.S. Cl. ........................... 623/23; 623/18
[58] Field of Search .......... 623/16, 18, 19, 21, 623/22, 23

[56] References Cited

U.S. PATENT DOCUMENTS

| | | | |
|---|---|---|---|
| 4,012,795 | 3/1977 | Doore et al. | |
| 4,032,994 | 7/1977 | Frey | |
| 4,058,856 | 11/1977 | Doerre et al. | |
| 4,268,919 | 5/1981 | Zeibig | 623/23 |
| 4,318,190 | 3/1982 | Cortesi | 623/23 |
| 4,687,488 | 8/1987 | Frey | |
| 4,842,605 | 6/1989 | Sonnerat et al. | |
| 4,921,500 | 5/1990 | Averill et al. | |
| 4,964,869 | 10/1990 | Auclair et al. | 623/23 |

FOREIGN PATENT DOCUMENTS

| | | |
|---|---|---|
| 0193681 | 9/1986 | European Pat. Off. |
| 2618763 | 11/1976 | Germany |
| 0011665 | 11/1978 | Germany |
| 3023354 | 4/1981 | Germany |
| 3802213 | 7/1989 | Germany |

Primary Examiner—David Isabella
Attorney, Agent, or Firm—Spensley Horn Jubas & Lubitz

[57] ABSTRACT

An artificial hip joint of the type wherein a metal stem is fitted into the tapered hall of a ceramic stem head via a tapered cone in the stem, the hip joint being characterized in that the tapered stem engages the tapered hall in the deeper portion of the tapered hall, whereby the compression strength (fracture load) of the stem head is improved. Deep engagement of the tapered stem within the tapered hall is accomplished by, for example, making the angle of the taper of the tapered cone slightly smaller than that of the tapered stem. Preferably, the angle of taper of the tapered cone is smaller than that of the tapered hall by about 40 minutes or less. In addition, the diameter at the base of the hall is enlarged to form a cavity.

11 Claims, 4 Drawing Sheets

ARTIFICIAL HIP JOINT

This is a continuation of application Ser. No. 07/370,450 filed on Jun. 23, 1989, now abandoned, which in turn is a continuation-in-part of Ser. No. 07/136,398, filed Dec. 22, 1987 now abandoned.

BACKGROUND OF THE INVENTION

1. Field of the Invention

This invention relates to an artificial hip joint adapted to replace and restore the hip joint of a human patient.

2. Prior Art

Artificial joints as heretofore used, and more particularly artificial hip joints, have comprised a stem head ball (hereinafter referred to as the stem head) integrally fixed to a stem or in tapered engagement with the stem by the use of metal such as stainless steel, cobalt chrome based alloy, or titanium alloy, in such a manner that the stem may be inserted into a femur by use of a cement in the gap between them. Sockets for receiving the stem head therein have been made of polyethylene and fixed to the pelvis with cement.

In recent years, general practice has been to use a construction in which the stem head is fixed to the end of a metal stem by tapered engagement. The kind of material used in such a construction has been primarily stainless steel, cobalt chromium alloy, or the like. An artificial joint formed from the material described is generally adapted to permit varying the height of the joint when the stem is fixed to the stem head by changing the depth and the diameter of the tapered hall. This type of joint system is becoming an element of the mainstream in artificial hip joint technology.

On the other hand, alumina ceramics low in friction and abrasion in combinations with polyethylene, especially Ultra High Molecular Weight Polyethylene (UHMWPE), have been recognized as suitable materials for the stem head, because of their excellent performance. They have been used in many cases. However, there is a tendency towards damage occurring to a ceramic stem head, due to improper engagement of the tapered portion (hereinafter referred to as the tapered cone) of the metal stem with the tapered hall of the ceramic stem head. It is said that a load up to about five times the body weight of a human being works on the condyle of a human hip joint, and accordingly a load of about 400 kg works on the condyle of a person with a body weight of 80 kg. The condyle is thus subjected to a relatively great force.

From the viewpoint of durability over a long period of time, a high coefficient of safety is also demanded of the hip joint. However, in actual practice, when the forward end of the stem is fitted into the tapered hall of the ceramic stem head, even a small lack of proper fit, caused for example by the presence of fine foreign matter straying into the gap between the hall and the end of the stem, could induce a crack of the stem head, posing a serious problem.

To solve the problems described above, it would according to one approach be necessary to bring the tapered hall formed in the stem head into complete tapered engagement with the tapered cone at the forward end of the stem. It is, however, virtually impossible to bring both into highly precise agreement with each other by machining, as both the tapered hall and the tapered cone are not perfectly round in most cases. Thus, it is a virtual practical impossibility to tightly fit the tapered cone into the tapered hall without forming a partial slit along the direction of the entire circumference of the fitting sphere and/or with respect to the entire length of the sphere.

In view of the circumstances above, there have been made various proposals, such as: circumferentially forming regularly-arranged concavities and convexities on the surface of the tapered cone of the metal stem (for example, according to Japanese Patent Laid-Open Publication No. 67693/1976); making the tapered cone of the stem hollow; or forming slits in the cone and deforming the tapered cone of the stem so as to bring the tapered cone of the stem into agreement with the tapered hall formed in the stem head.

Nonetheless, it has to date proved impossible to prevent entirely development of cracks in the ceramic stem head and the resultant reduction in joint strength even by the expedients described above. Accordingly, the means proposed to date have not been sufficient to provide a joint in which one may place perfect trust as to its extended function in restoration of the human body.

SUMMARY OF THE INVENTION

In an effort to solve the above problems, this invention is intended to prevent cracks in the stem head and increase the compression strength of the stem head by bringing the forward end portion of the tapered cone into engagement with the tapered hall at a relatively deep position, preferably the engagement occurs at a position deeper than about one half of the depth of the tapered hall. This can be accomplished by making the angle of taper of the tapered cone of the stem slightly smaller than the angle of taper of the tapered hall in the ceramic stem head. Alternatively, the tapered hall may be provided with an enlarged diameter along the shallowest approximately one half of its length or the tapered cone may be provided with a diminished diameter along a corresponding portion of its length. Any of these configurations, alone or in combination, can be used to bring the tapered cone into engagement with the tapered hall in the deepest approximately one half of the tapered hall and thereby increase the compression strength of the stem head. In addition, the base (i.e., the deepest portion) of the hall is enlarged relative to the diameter of the hall, thereby forming a cavity which serves to avoid concentrations of mechanical stress at the base of the hall.

DETAILED DESCRIPTION OF THE INVENTION

A description will now be given of embodiments of the invention with reference to the drawings.

Figure 1:
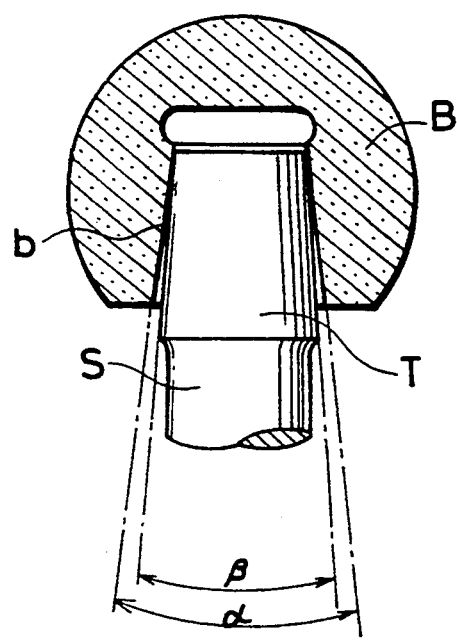
FIGS. 1, 2 and 3 show sectional views of artificial hip joints embodying the invention.

In FIG. 1, the character B designates a stem head, made of ceramics such as alumina, zirconia and the like, which stem head is rotatably received in a socket (not shown). The stem head B is formed with a tapered hall $\underline{b}$. The character S designates a stem to be insertedly fixed to the femur, the stem being made of metal such as titanium alloy or stainless steel, and formed at the forward end portion with a tapered cone T. The stem head B is mounted on the top end of the stem S via the tapered cone T, which is fitted into the tapered hall $\underline{b}$ of the stem head B at a point as described below.

In this case, the respective angles of taper $\alpha$ and $\beta$ of the tapered hall $\underline{b}$ and tapered cone T are formed so as to be of various angles. When fixing force (fitting force) and rotation resisting force provided by a combination of the angles are measured, $\alpha \cong \beta \cong$ about 6° is optimal, such that the angle of taper $\alpha$ of the tapered hall of the stem head B is larger by about 40 minutes or less, preferably about 2–40 minutes, than the angle of taper of the tapered cone T of the stem S. The tapered cone T is inserted to a point where it is brought into engagement at a relatively deeper position of the tapered hall $\underline{b}$ than if the respective tapers were identical by a combination of stem head B and stem S whose angles of taper $\alpha$ and $\beta$ are placed in the appropriate relationship. In particular, the cone is generally inserted to a position deeper than about one half the depth of the tapered hall.

Figure 2:
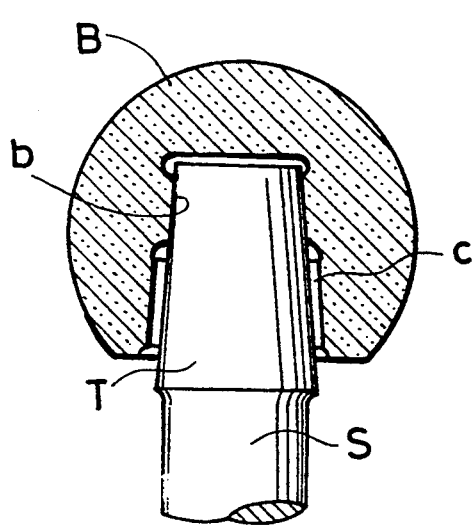

In the embodiment shown in FIG. 2, when the tapered cone T of the stem S is fitted into the tapered hall $\underline{b}$ of the stem head B by diametrally enlarging a tapered hall C in concentric relation with the hall $\underline{b}$ to a vicinity of about half the depth of the tapered hall $\underline{b}$, it is possible to bring the tapered cone T insertedly into contact with only the tapered hall $\underline{b}$ of small diameter in the front end position.

Figure 3:
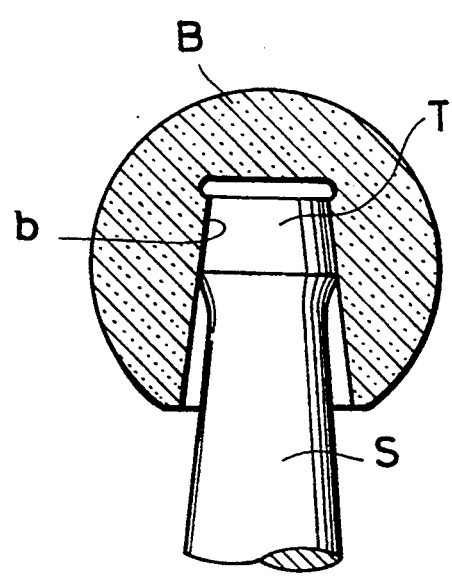

Further, in the embodiment shown in FIG. 3, the tapered cone T may be formed at the forward end of the stem S so as to permit engagement of the stem with only the deeper portion of the tapered hall.

The above preferred degree of engagement is inferred, from the the results of a fatigue test reported below and from a breaking test carried out subsequent to the fatigue test, to be such that in most assemblies, the stem head does not rotate or slide with respect to the tapered cone. Moreover, when a fatigue test subjecting the system to the equivalent of an estimated average value of many years (for example, 20 or 30 years) of accumulated articulation momentum of the hip joint in a human body is repeatedly performed with the head assembled together with the tapered cone, the stem head is found to be only slightly moved or deformed inside the tapered hall.

Figure 4A:
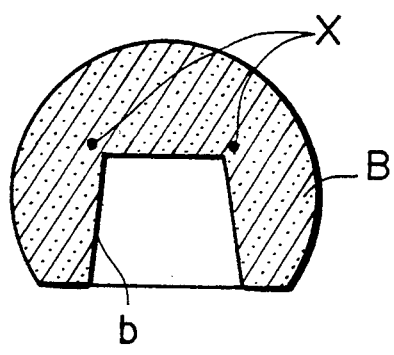
FIGS. 4(A) and 4(B) illustrate the shape of the base of prior art and inventive halls, respectively.

Further according to another embodiment of the present invention, the diameter at the base of the female portion of the joint (i.e., the hall) is enlarged to form a cavity. This enlargement is carried out in order to avoid a concentration of mechanical stress at the points x identified in FIG. 4(A) for a hall in accordance with the prior art. Such mechanical stress concentrations may cause fissures or cracks at the corners of the base of the female portion. In addition, the enlargement as illustrated in FIG. 4(B) serves as an escapement for a tapering tool movement (generally, a diamond-coated tool) when the tool tip reaches the bottom of the female portion during the processing of the taper, as illustrated in FIGS. 5(A)–5(C).

Figure 4B:
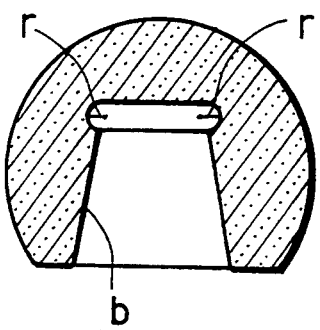

As further illustrated in FIG. 4(B), the enlargement at the base of the female portion has a radius of curvature r of the full semicircular arc of the enlargement at its deepest position. Preferably, r is within the range of 1.0 mm–3.0 mm. It has been determined by experiment that radii of curvature less than about 1.0 mm or greater than about 3.0 mm do not substantially prevent the generation of fissures or cracks due to mechanical stress.

Figure 5A:
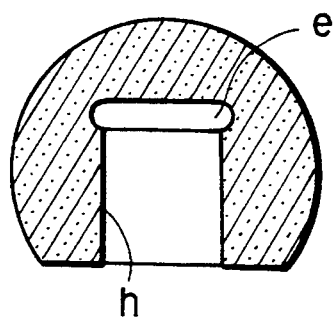
FIGS. 5(A), 5(B) and 5(C) progressively illustrate stages in a preferred process for preparation of a hall according to the present invention.
Figure 5B:
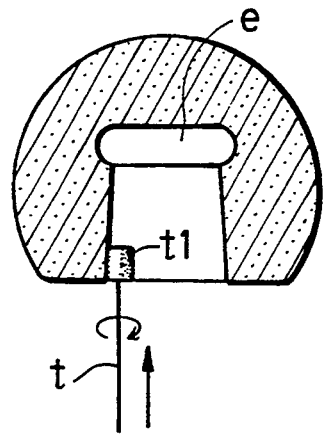
Figure 5C:
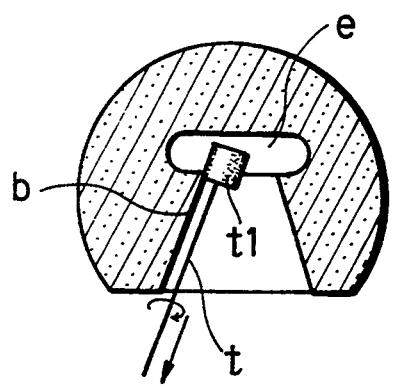

In a preferred aspect of the invention, the tapered hall is generated by a method as generally depicted in FIGS. 5(A)–5(C). First, the stem head ball is provided with a straight, cylindrical hall h, as illustrated in FIG. 5(A), and the enlargement e at the base of the female portion is introduced by known methods. Next, a rotational tapering tool t is inserted into the hall and employed to effect tapering from the outside perimeter of the hall towards the interior, as shown in FIG. 5(B). When the bottom of the tip has reached the base of the hall, as illustrated in FIG. 5(C), the tip is moved in retrograde to effect reciprocal processing (i.e., from the interior of the hall to the outside perimeter). It should of course be realized that alternative processing methods for generating the tapered hall may also be employed.

In the event that an escapement is unnecessary or undesirable, stress concentrations can still be reduced by forming a curved, rather then sharp, transition between the side of the tapered hall and the base of the tapered hall. As described above, the radius of curvature for the transition should be within the range of 1.0 mm–3.0 mm. In this configuration, stress concentrations are reduced without providing an enlarged diameter at the base of the tapered hall.

When, as shown in the embodiments of FIG. 1, the angles of taper of the tapered hall $\underline{b}$ and tapered cone T are adjusted, the tapered cone T is designed to make engagement with the hall $\underline{b}$ at a point deeper than at least half the depth of the hall $\underline{b}$, so that the compression strength (fracture load) of the stem head B in the tapered hall $\underline{b}$ fitted over the tapered cone is increased, as shown in Table 1 with respect to samples in which the outer diameters of the stem head and inner diameters of the hall are the same, respectively.

TABLE 1

| Difference between angles of taper $\alpha$, $\beta$ ($\alpha - \beta$) (degree) (average value of 10 samples) | Maximum compression strength (KN) |
| --- | --- |
| 0.16 | 60 |
| −0.008 | 23 |

The compression strength of the inventive arrangement shown is about 2.6 times as high as that of conventional products.

The technical reason why a difference in the angle of taper, and thus the engagement of the tapered stem at a position relatively deep within the tapered hall, as described provides an improvement in the compression strength of the ceramic stem head as demonstrated by these findings is not entirely theoretically clear. A test conducted by way of experiment on a metal stem head and metal stem under entirely the same conditions did not reveal that the angle of taper improved the compression strength of the metal stem head. This appears to present a strong contrast with the above findings.

Another interesting effect of differences in angles of taper α-β of varying magnitudes on the compression strength of ceramic stem heads of the same diameter is shown by the results of a second compression test.

Second compression test

Figure 6A:
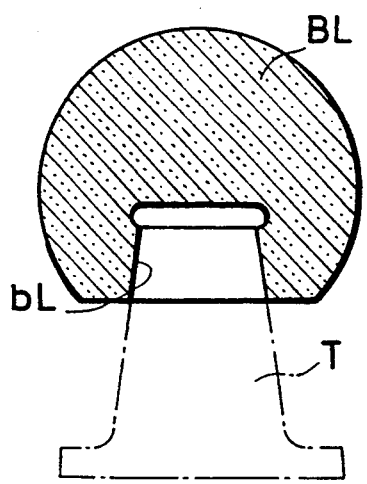
FIGS. 6(A), 6(B) and 6(C) are sectional views of three kinds of stem head which are employed in the second compression test of the invention.
Figure 6B:
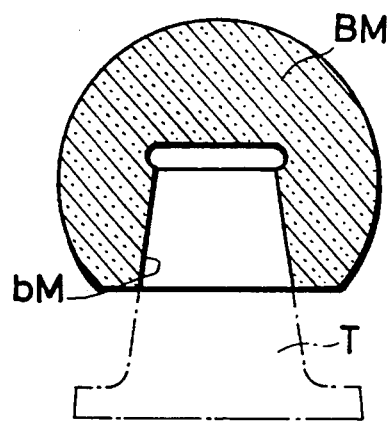
Figure 7:
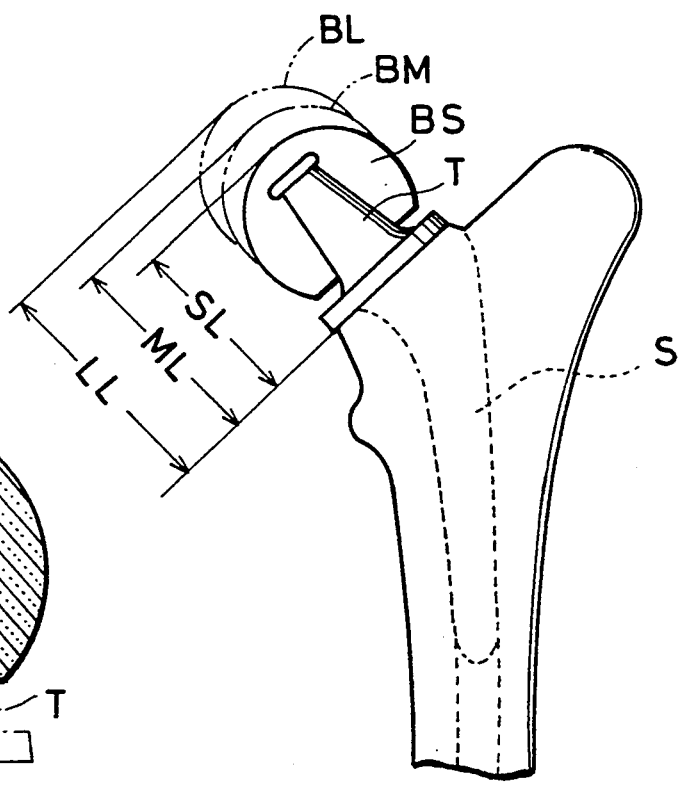
FIG. 7 is a view illustrating the length of stem neck when a metal stem is fitted into the stem head.
Figure 6C:
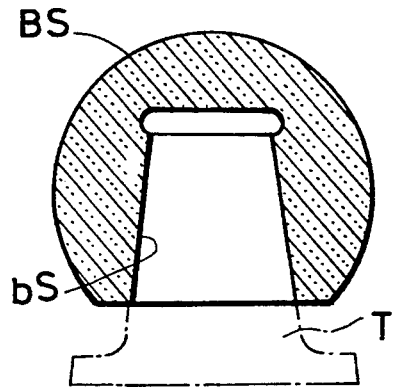

Three kinds of alumina ceramic stem heads BL, BM and BS (as shown in FIGS. 6(a), 6(b) and 6(c)) with constant angles of taper α of the tapered hall b, but each different in the depths LL, ML and SL of the tapered hall b, were employed. As shown in FIG. 7, when the metal stem heads T (with a constant angle of taperβ) are fitted into the stem heads BL, BM and BS, the length of the stem neck is reduced successively from large to small (LL, ML and SL as shown in FIG. 7). Under these conditions, $α - β = \Theta(°)$. For test purposes, values for changes in the taper angles were selected. The relevant equations for the selected values become $\Theta = 0' = 2' = \Theta_2$, wherein 0' is excluded, and $\Theta = 1' - 7' = \Theta_7$. Combinations of the stem heads BL, BM and BS with differences in the angle of taper are indicated as follows.

Figure 8:
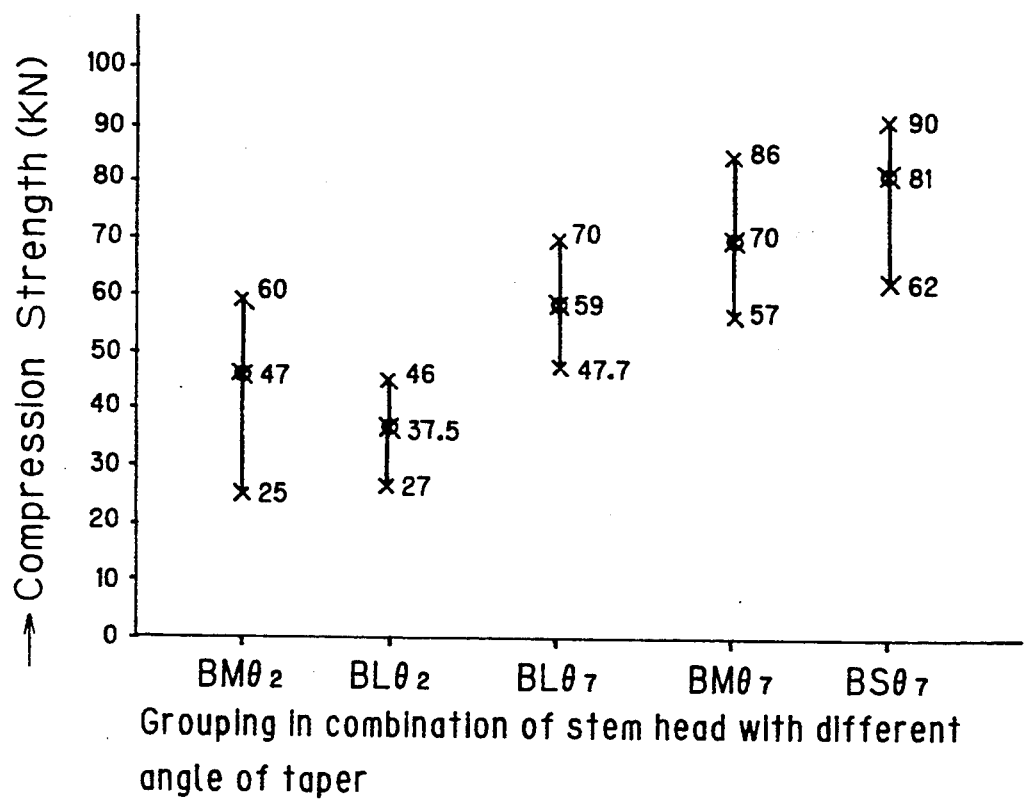
FIG. 8 is a graphic representation showing the results of the second compression test and illustrating the relationship between various combinations of stem head with differences in angles of taper and the compression strength observed for the combinations.

Example:

A combination of stem head BM with $\Theta_2$ (0'−2) is represented by BMΘ₂. In accordance with this expression, FIG. 8 shows the relationship between compression strength and combinations of the various stem heads BL, BM and BS with Θ. In FIG. 8, the character 8 indicates an average value. As apparent from FIG. 8, in the stem head BM, $$\frac{\theta_7}{\theta_2} = \frac{70}{47} = 1.489 \text{ (times)}$$

while in the stem head BL, $$\frac{\theta_7}{\theta_2} = \frac{59}{37.5} = 1.573 \text{ (times)}$$

It is apparent that there is a great difference in compression strength of the stem head between the angles of taper 0'−2' and 1'−7', respectively, and the improvement in compression strength becomes marked in proportion to an increase in the difference between angles of taper α−β. No test was conducted on BS Θ₂.

With an inventive joint constructed such that when the tapered cone at the end of the stem is insertedly fixed to the tapered hall formed in the stem head by connecting the ceramic stem head to the metal stem, the tapered cone T is brought into engagement with the front end surface at a depth greater than about half the depth of the tapered hall, i) the compression strength of the stem head can be greatly increased; ii) there is no need to provide engagement between the entire tapered surfaces, with the result that control over production is greatly facilitated; iii) production is further facilitated because there is no need to form groove-like irregularities and slits in the tapered surface at the forward end portion of the stem, nor to make the tapered cone of the stem hollow; iv) the stem head may be formed with a small diameter, with the result that the wall thickness of high density polyethylene or the like which forms the slide face of the socket for receiving the head may be sufficiently large to enable a prolongation of the service life (longevity) of the joint; and v) the area of contact of the tapered surfaces with each other is smaller, so that high precision machining of a narrower area is all that is necessary. Thus, the invention makes it possible to reduce machining and production cost, while providing a superior product.

Accordingly, the invention renders it possible to provide an artificial hip joint having high strength, long service life, decreased production costs and high fidelity, and makes a great contribution toward the good of mankind.

What is claimed is:

1. An artificial hip joint comprising:
    a ceramic head having a tapered female cavity, said cavity tapering from an open end inwardly to a base disposed within the head, said cavity being subdivided into approximately two halves, one approximate half being a deeper approximate half located adjacent the base as compared with the open end; and
    a metal stem having a tapered cone so that said tapered engagement occurs only in the deeper approximate half of the tapered female cavity when the ceramic head and the metal stem are fully connected to each other.

2. An artificial hip joint according to claim 1, wherein the taper of the cone is made slightly smaller than that of the tapered female cavity 3. An artificial hip joint according to claim 1, wherein the ceramic head is formed with a hall having a large diameter concentric with said tapered female cavity and extending to a vicinity of about half the depth of said tapered female cavity.

4. An artificial hip joint according to claim 1, wherein said tapered cone has a reduced diameter below a portion brought into engagement with the deepest approximately one half of said tapered female cavity.

5. An artificial hip joint including a ceramic head having a tapered female cavity, said female cavity tapering from an open end inwardly to a base disposed within the head; and
    a metal stem having a tapered cone configured to be fitted into the tapered female cavity, the tapered cone having a forward end portion, wherein the angle of taper of said tapered cone is slightly smaller than that of said tapered female cavity so that when the metal stem is fully connected to the ceramic head by bringing the tapered cone into tapered engagement with the tapered female cavity, only the forward end portion of said tapered cone of the stem is brought into engagement with said tapered female cavity at a deeper position in the tapered female cavity than if the respective angles of taper were the same, thereby increasing the compression strength of said stem head.

6. An artificial hip joint according to claim 5, wherein the angle of taper of said tapered female cavity is larger than that of said tapered cone of the stem by an amount greater than 0' and less than or equal to about 40".

7. An artificial hip joint according to claim 5, wherein said deeper position of said tapered female cavity is greater than about half of the depth of said tapered female cavity.

8. An artificial hip joint according to claim 5, wherein the base of said tapered female cavity is enlarged relative to the diameter of the base of the female cavity, thereby forming a cavity which serves to avoid concentrations of mechanical stress at the base of the female cavity.

9. An artificial hip joint according to claim 7, wherein said tapered female cavity and said tapered cone have substantially smooth contact surfaces for reducing friction therebetween.

10. An artificial hip joint according to claim 8, wherein said cavity has a radius of curvature r which is between about 1.0 and about 3.0 mm.

11. An artificial hip joint comprising:
 a ceramic head having a tapered female cavity, said tapered female cavity tapering from an open end inwardly to a base disposed within said head, said cavity being subdivided into approximately two halves, one approximate half being a deeper approximate half located adjacent the base as compared with the open end; and
 a metal stem having a tapered male portion secured in said ceramic head, said tapered male portion having a tapered contact surface area for tapered engagement with said tapered female cavity adjacent said base wherein said contact surface area is located only in the deeper approximate half of said tapered female cavity when the ceramic head and the metal stem are fully connected to each other.

* * * * *

UNITED STATES PATENT AND TRADEMARK OFFICE
CERTIFICATE OF CORRECTION

PATENT NO. : 5,413,610
DATED : May 9, 1995
INVENTOR(S) : Hirokazu Amino, Yoshinori Shiraiwa, Ian C. Clarke It is certified that error appears in the above-indentified patent and that said Letters Patent is hereby corrected as shown below:

Claim 6, column 6, line 58, please change "about 40"." to --about 40'.--.

Signed and Sealed this

Twenty-third Day of July, 1996

Attest:

BRUCE LEHMAN

Attesting Officer        Commissioner of Patents and Trademarks